US010271718B2

(12) United States Patent
Wataya et al.

(10) Patent No.: US 10,271,718 B2
(45) Date of Patent: Apr. 30, 2019

(54) IMAGE PICKUP UNIT AND ENDOSCOPE (71) Applicant: OLYMPUS CORPORATION, Tokyo (JP)

(72) Inventors: Yuichi Wataya, Akiruno (JP); Akira Muramatsu, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/609,096

(22) Filed: May 31, 2017

(65) Prior Publication Data
US 2017/0265729 A1 Sep. 21, 2017

Related U.S. Application Data (63) Continuation of application No. PCT/JP2016/061763, filed on Apr. 12, 2016.

(30) Foreign Application Priority Data

Jul. 23, 2015 (JP) ................ 2015-145972

(51) Int. Cl.
A61B 1/00 (2006.01)
A61B 1/04 (2006.01)
(Continued)

(52) U.S. Cl.
CPC ............ A61B 1/04 (2013.01); A61B 1/00009 (2013.01); A61B 1/00188 (2013.01);
(Continued)

(58) Field of Classification Search
CPC ... G02B 23/26; G02B 23/2484; G02B 23/243
See application file for complete search history.

(56) References Cited

U.S. PATENT DOCUMENTS

2004/0008421 A1 1/2004 Yoshida et al.
2009/0303619 A1* 12/2009 Iwasaki ................ A61B 1/0008
359/811
2013/0083182 A1* 4/2013 Kitano ..................... G02B 7/10
348/76

FOREIGN PATENT DOCUMENTS

EP 2072001 A2 6/2009
EP 2 130 482 A1 12/2009
(Continued)

OTHER PUBLICATIONS

International Search Report dated Jul. 12, 2016 issued in PCT/JP2016/061763.
(Continued)

Primary Examiner — Timothy J Neal
(74) Attorney, Agent, or Firm — Scully, Scott, Murphy & Presser, P.C.

(57) ABSTRACT

An image pickup unit includes: a focus switching type observation optical system including fixed lenses and a moving lens; fixed frames that hold the fixed lenses; a moving frame that is arranged to be movable back and forth in a direction along a photographing optical axis of the observation optical system and holds the moving lens; and a correction frame fixed in the fixed frames, configured to house the moving frame such that the moving frame can advance and retract, including a stopper that abuts the moving frame to restrict movement in one direction of the photographing optical axis, and being slightly adjustable to realize one of focal lengths of the observation optical system.

7 Claims, 8 Drawing Sheets (51) Int. Cl.
 *G02B 23/26* (2006.01)
 *A61B 1/05* (2006.01)
 *G02B 23/24* (2006.01)

(52) U.S. Cl.
 CPC .......... *G02B 23/26* (2013.01); *A61B 1/00096* (2013.01); *A61B 1/00163* (2013.01); *A61B 1/05* (2013.01); *G02B 23/243* (2013.01); *G02B 23/2484* (2013.01)

(56) References Cited

FOREIGN PATENT DOCUMENTS

| | | |
|---|---|---|
| JP | S63-068807 A | 3/1988 |
| JP | 2004-016337 A | 1/2004 |
| JP | 2009-148369 A | 7/2009 |
| JP | 2009-300761 A | 12/2009 |
| JP | 5394462 B2 | 1/2014 |
| JP | 2015-112336 A | 6/2015 |

OTHER PUBLICATIONS

Extended Supplementary European Search Report dated Jul. 19, 2018 in European Patent Application No. 16 82 7473.6.

\* cited by examiner

IMAGE PICKUP UNIT AND ENDOSCOPE

CROSS REFERENCE TO RELATED APPLICATION

This application is a continuation application of PCT/JP2016/061763 filed on Apr. 12, 2016 and claims benefit of Japanese Application No. 2015-145972 filed in Japan on Jul. 23, 2015, the entire contents of which are incorporated herein by this reference.

BACKGROUND OF INVENTION

1. Field of the Invention

The present invention relates to an image pickup unit capable of changing an optical characteristic of an observation optical system and an endoscope provided with the image pickup unit.

2. Description of the Related Art

As is well known, an endoscope is widely used, for example, to observe or treat inside of a living body (inside of a body cavity) or to inspect or repair industrial plant equipment.

In recent years, in some endoscopes of this type, an image pickup unit capable of moving an observation optical system in a photographing optical axis direction to change a focal length has been used for a zooming function of adjusting focus of a photographing image or adjusting magnification of wide/tele and the like. Note that the technique of the image pickup unit capable of changing the focal length is used not only in the endoscopes, but also in various photography devices.

For example, an image pickup unit is known as disclosed in Japanese Patent Application Laid-Open Publication No. 2004-16337, the image pickup unit including an actuator for a focus switching system, the image pickup unit being configured to drive a moving lens unit (moving lens frame) provided in an observation optical system.

In such a focus switching type image pickup unit, relative positions of each fixed lens frame and the like generally need to be slightly adjusted during assembly of the image pickup unit in relation to an advance position of the moving lens frame in order to realize an appropriate focus state even if there are machining tolerances in each lens frame, each objective lens, and the like.

Therefore, a technique of an image pickup apparatus is disclosed for example in Japanese Patent Application Laid-Open Publication No. 2009-300761, the image pickup apparatus capable of simply making a slight adjustment to a predetermined set angle of view even if there are machining tolerances in components and variations of clearance in moving lens frames fitted to lens frames.

By the way, assembly accuracy of an objective optical system needs to be drastically improved in a recent image pickup apparatus along with shrinking of an image pitch of an image pickup device.

SUMMARY OF THE INVENTION

An aspect of the present invention provides an image pickup unit including: an observation optical system including a fixed lens and a moving lens; a fixed frame that holds the fixed lens; a moving frame that is arranged to be movable back and forth in a direction along a photographing optical axis of the observation optical system and holds the moving lens; and a correction frame fixed in the fixed frame, configured to house the moving frame such that the moving frame can advance and retract, including a stopper configured to abut the moving frame to restrict movement in one direction of the photographing optical axis, and being adjustable to realize one of focal lengths of the observation optical system.

An aspect of the present invention provides an endoscope including an image pickup unit on a distal end portion of an insertion portion inserted into a subject, the image pickup unit including: an observation optical system including a fixed lens and a moving lens; a fixed frame that holds the fixed lens; a moving frame that is arranged to be movable back and forth in a direction along a photographing optical axis of the observation optical system and holds the moving lens; and a correction frame fixed in the fixed frame, configured to house the moving frame such that the moving frame can advance and retract, including a stopper configured to abut the moving frame to restrict movement in one direction of the photographing optical axis, and being adjustable to realize one of focal lengths of the observation optical system.

DETAILED DESCRIPTION OF THE PREFERRED EMBODIMENT(S)

Figure 1:
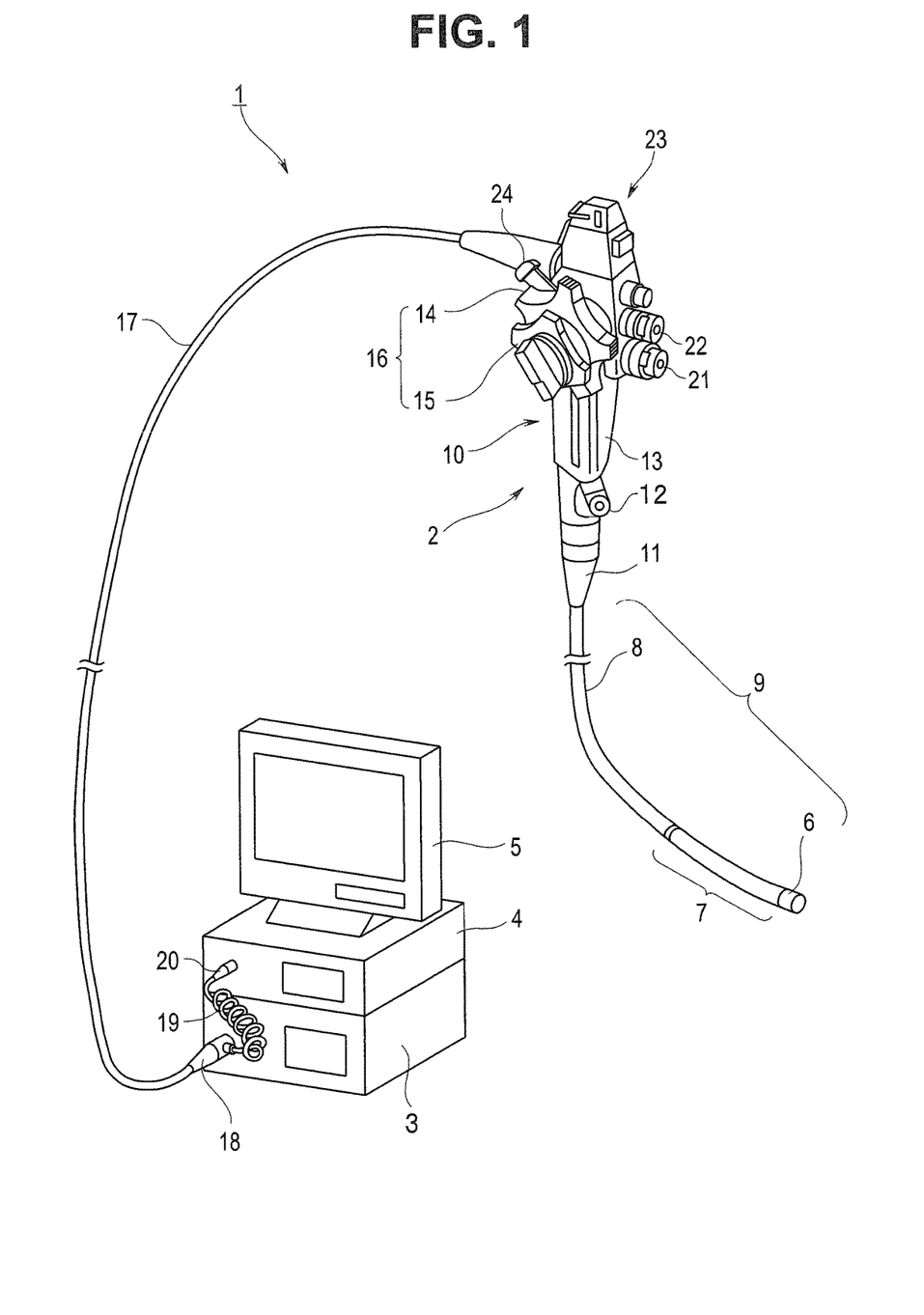
FIG. 1 is an explanatory view showing an overall configuration of an endoscope according to an aspect of the present invention.
Figure 2:
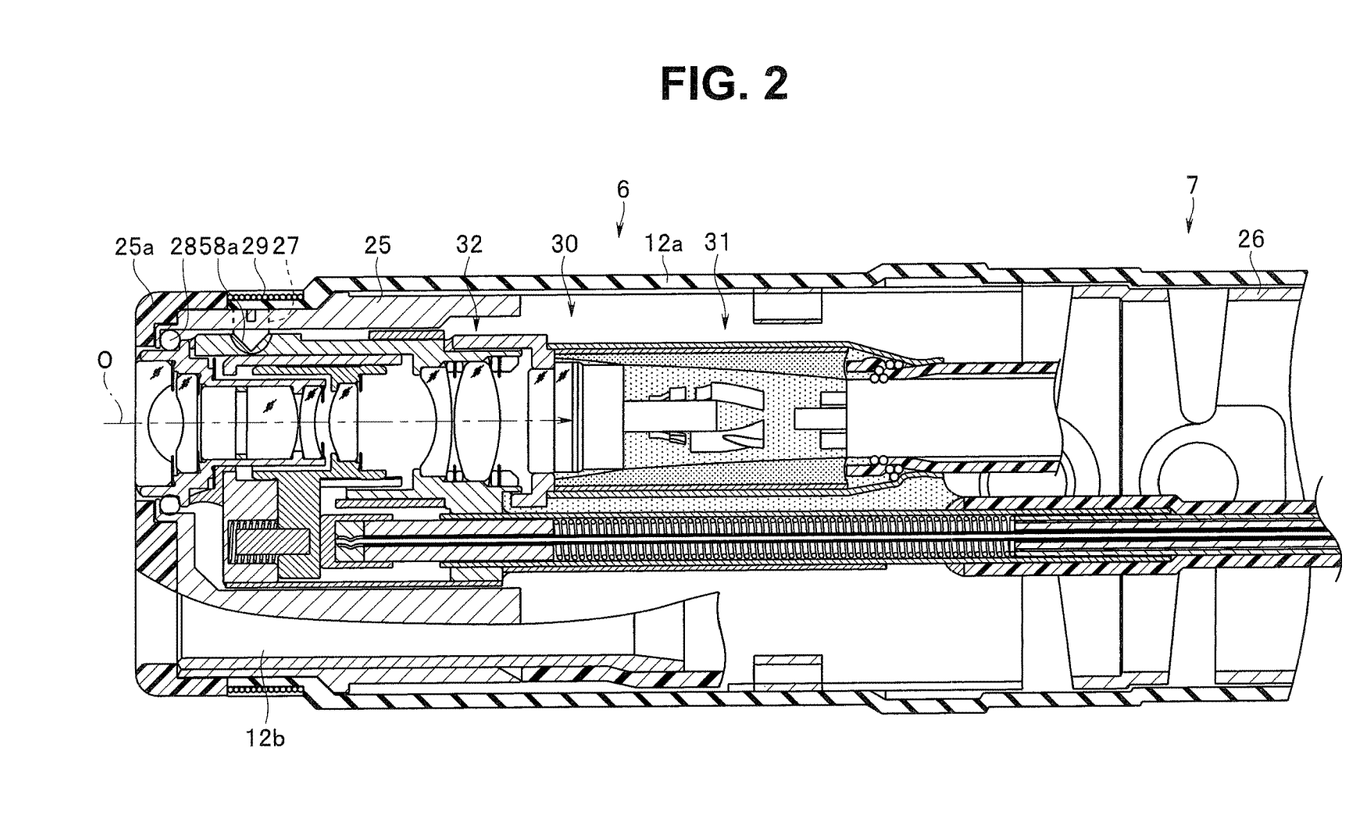
FIG. 2 is a cross-sectional view of an internal configuration of a distal end portion and a bending portion according to the aspect of the present invention.

Hereinafter, a mode of the present invention will be described with reference to the drawings. FIG. 1 is an explanatory view showing an overall configuration of an endoscope according to an aspect of the present invention. FIG. 2 is a cross-sectional view showing an internal configuration of a distal end portion and a bending portion. FIG.

Figure 5:
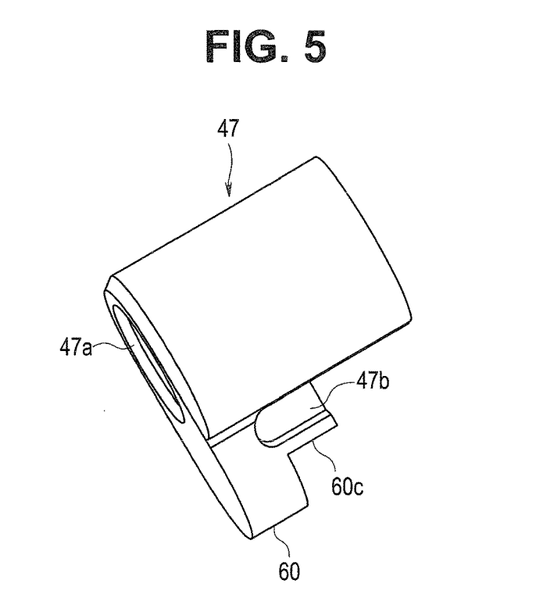
FIG. 5 is a perspective view showing a configuration of a moving lens position correction frame as viewed from one direction according to the aspect of the present invention.
Figure 6:
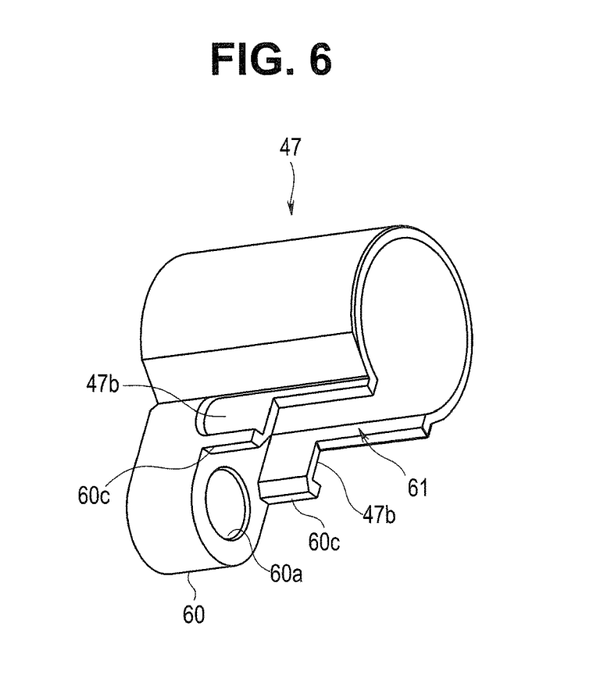
FIG. 6 is a perspective view showing a configuration of the moving lens position correction frame as viewed from another direction according to the aspect of the present invention.
Figure 7:
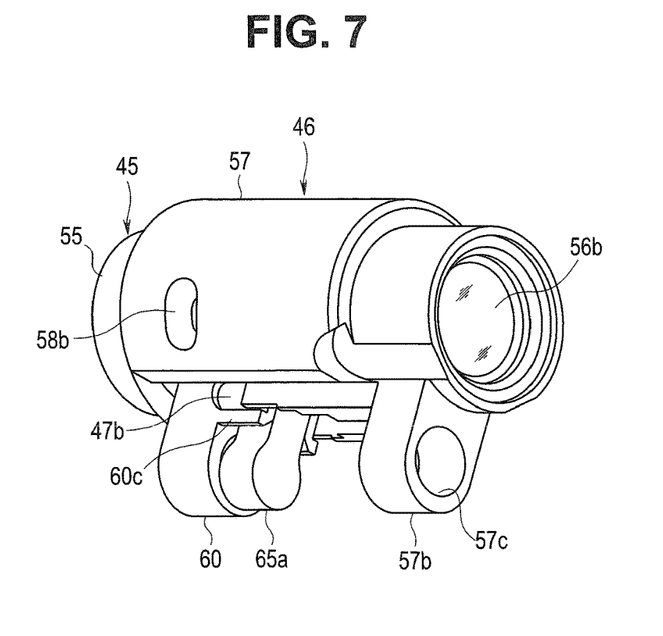
FIG. 7 is a perspective view showing an assembled state of a front lens group unit and a back lens group unit housing the moving lens position correction frame and the moving lens unit according to the aspect of the present invention.
Figure 8:
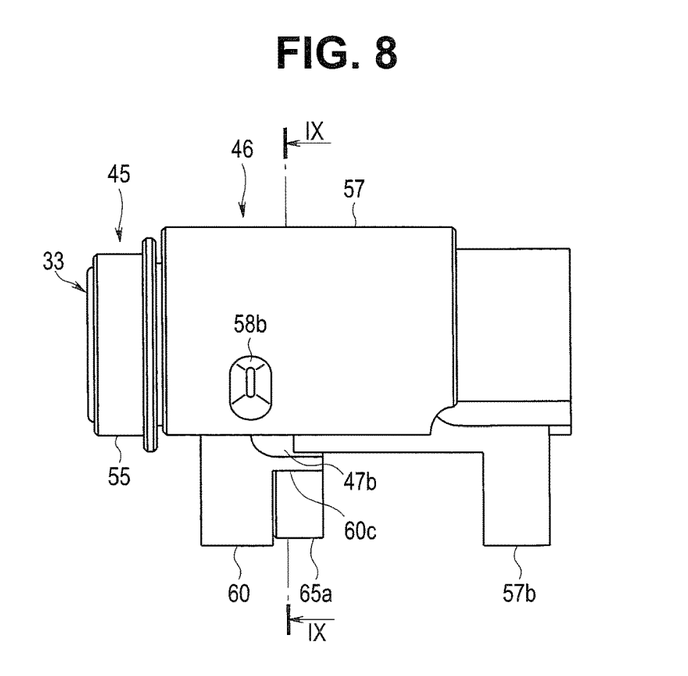
FIG. 8 is a side view showing an assembled state of the front lens group unit and the back lens group unit housing the moving lens position correction frame and the moving lens unit according to the aspect of the present invention.
Figure 9:
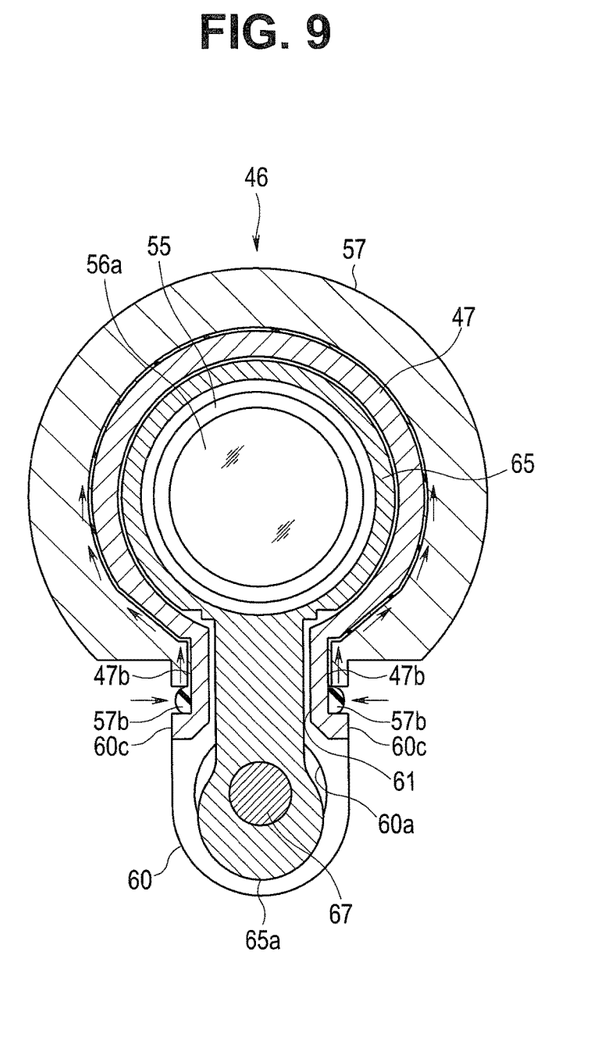
FIG. 9 is a cross-sectional view of a line IX-IX of FIG. 8 according to the aspect of the present invention.
Figure 10:
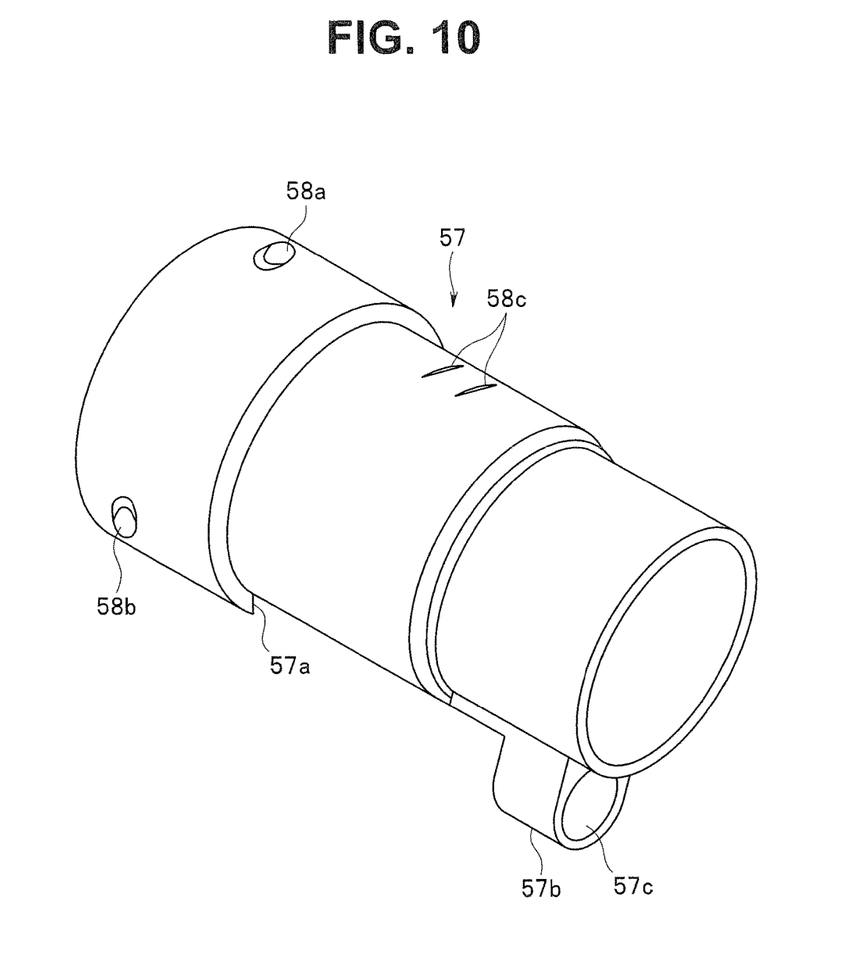
FIG. 10 is a perspective view showing a configuration of the back lens group frame according to the aspect of the present invention.

3 is a cross-sectional view showing a configuration of an image pickup unit in a state in which a moving lens unit is moved to a front advance position. FIG. 4 is cross-sectional view showing a configuration of the image pickup unit in a state in which the moving lens unit is moved to a back retraction position. FIG. 5 is a perspective view showing a configuration of a moving lens position correction frame as viewed from one direction. FIG. 6 is a perspective view showing a configuration of the moving lens position correction frame as viewed from another direction. FIG. 7 is a perspective view showing an assembled state of a front lens group unit and a back lens group unit housing the moving lens position correction frame and the moving lens unit. FIG. 8 is a side view showing an assembled state of the front lens group unit and the back lens group unit housing the moving lens position correction frame and the moving lens unit. FIG. 9 is a cross-sectional view of a line IX-IX of FIG. 8. FIG. 10 is a perspective view showing a configuration of the back lens group frame.

As shown in FIG. 1, an electronic endoscope system (hereinafter, simply called an endoscope system) 1 of the present embodiment is configured by electrically connecting an electronic endoscope apparatus (hereinafter, simply called an endoscope) 2 as an endoscope, a light source apparatus 3, a video processor 4, and a color monitor 5.

The endoscope 2 includes an insertion portion 9 and an operation portion 10 from which the insertion portion 9 is extended, and a universal cord 17 extended from the operation portion 10 is connected to the light source apparatus 3 through a scope connector 18.

A coiled scope cable 19 is extended from the scope connector 18. An electrical connector portion 20 is provided on the other end side of the scope cable 19, and the electrical connector portion 20 is connected to the video processor 4.

The insertion portion 9 is configured by continuously providing a distal end portion 6, a bending portion 7 and a flexible tube portion 8 in order from a distal end side. A well-known distal end opening portion, an observation window, a plurality of illumination windows, an observation window cleaning port, and an observation object cleaning port (all of which are not shown) are arranged on a distal end surface of the distal end portion 6.

On a back surface side of the observation window, an image pickup unit described later is arranged in the distal end portion 6. A distal end side of a light guide bundle not shown is arranged on a back surface side of the plurality of illumination windows.

The light guide bundle is inserted and disposed inside of the universal cord 17 from the insertion portion 9 and through the operation portion 10, and the light guide bundle can transmit illumination light from the light source apparatus 3 to the illumination windows when the scope connector 18 is connected to the light source apparatus 3.

The observation window cleaning port and the observation object cleaning port configure opening portions of two cleaning tubes not shown that are inserted into the universal cord 17 from the distal end portion 6.

The cleaning tubes are connected to a cleaning tank that reserves cleaning water and to a compressor (neither is shown) on the light source apparatus 3 side.

The operation portion 10 is provided with: a bend preventing portion 11 from which the insertion portion 9 extends; a forceps port 12 arranged on a side portion on a lower side; an operation portion body 13 configuring a grip portion of a middle part; a bending operation portion 16 including two bending operation knobs 14 and 15 provided on an upper side; an air/water feeding control portion 21; a suction control portion 22; a switch portion 23 including a plurality of switches and configured to mainly operate an image pickup function; and an operation lever 24 for performing advance and retraction operation of a moving lens provided in the image pickup unit described later to operate, for example, a focusing function of adjusting the focus and a zooming function of adjusting the magnification of wide/tele or the like.

Note that the forceps port 12 of the operation portion 10 configures an opening portion of a treatment instrument channel not shown that is mainly inserted and disposed in the insertion portion 9 up to the distal end opening portion of the distal end portion 6.

Next, a configuration of the distal end portion 6 of the endoscope 2 will be mainly described based on FIG. 2.

As shown in FIG. 2, an image pickup unit 30 is arranged inside of the distal end portion 6.

The image pickup unit 30 is inserted and fitted to a rigid distal end rigid member 25 and is fixed to the distal end rigid member 25 through a set screw 27 from a lateral direction.

An O-shaped ring 28 for securing water tightness with the distal end rigid member 25 is arranged on an outer circumference portion on a distal end side of the image pickup unit 30. A distal end cover 25a configuring the distal end surface of the distal end portion 6 is adhered and fixed to a distal end side of the distal end rigid member 25.

Note that a distal end opening portion that is a hole portion formed on the distal end cover 25a configures an opening portion of a treatment instrument channel 12b in the distal end portion 6 as described above.

A plurality of bending pieces 26 configuring the bending portion 7 are continuously provided on a proximal end side of the distal end rigid member 25, and outer circumferences of the distal end rigid member 25 and the bending pieces 26 are integrally covered by a distal end insertion portion rubber member 12a. A distal end outer circumference portion of the distal end insertion portion rubber member 12a is fixed to the distal end rigid member 25 through a spool adhesion portion 29.

Note that the members, such as the cleaning tube, the light guide bundle for illumination, and the like, arranged on the distal end portion 6 are conventionally well-known components, and the members will not be described.

Next, a detailed configuration of the image pickup unit 30 will be described based on FIGS. 3 to 5.

Figure 3:
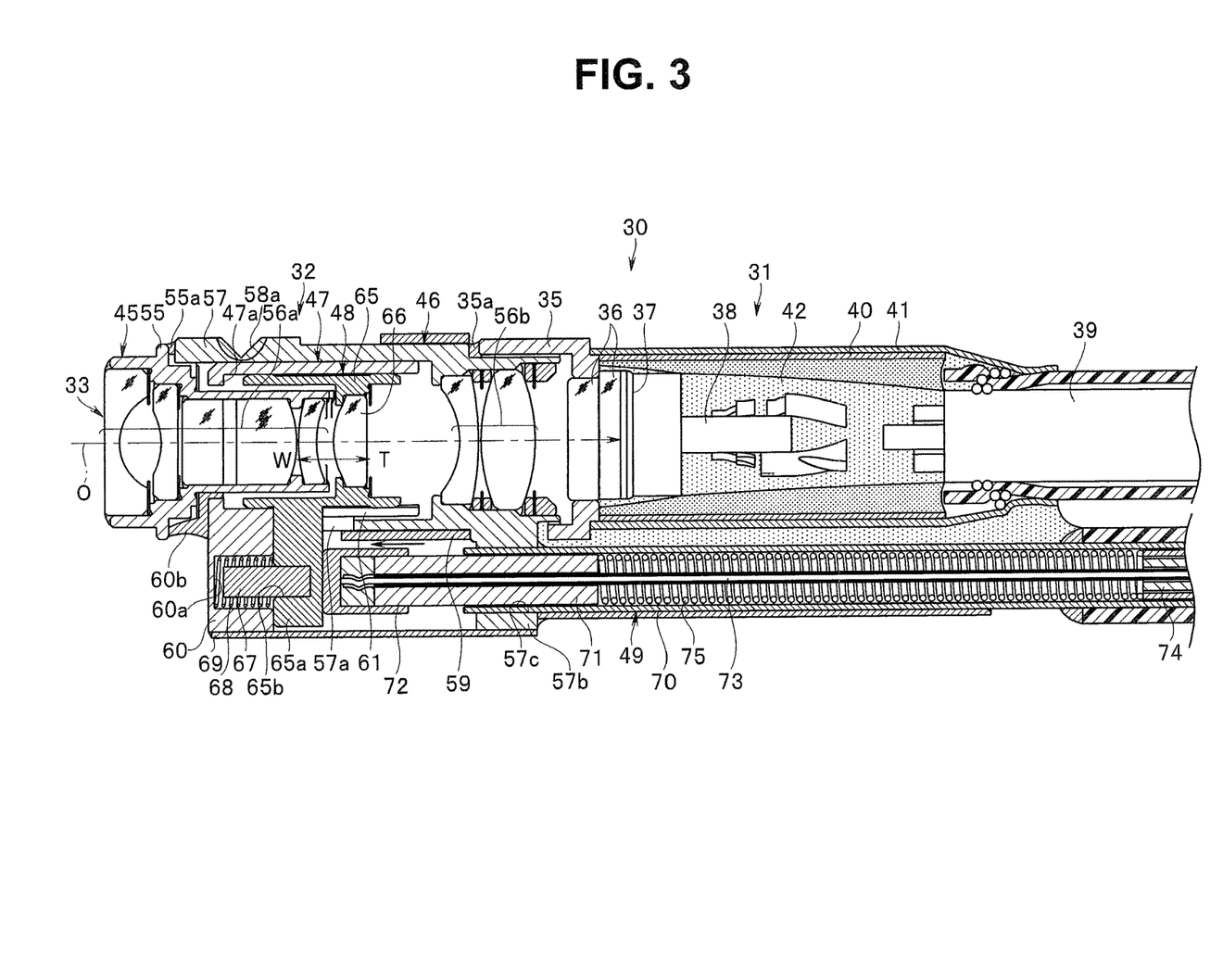
FIG. 3 is a cross-sectional view showing a configuration of an image pickup unit of a state in which a moving lens unit is moved to a front advance position according to the aspect of the present invention.
Figure 4:
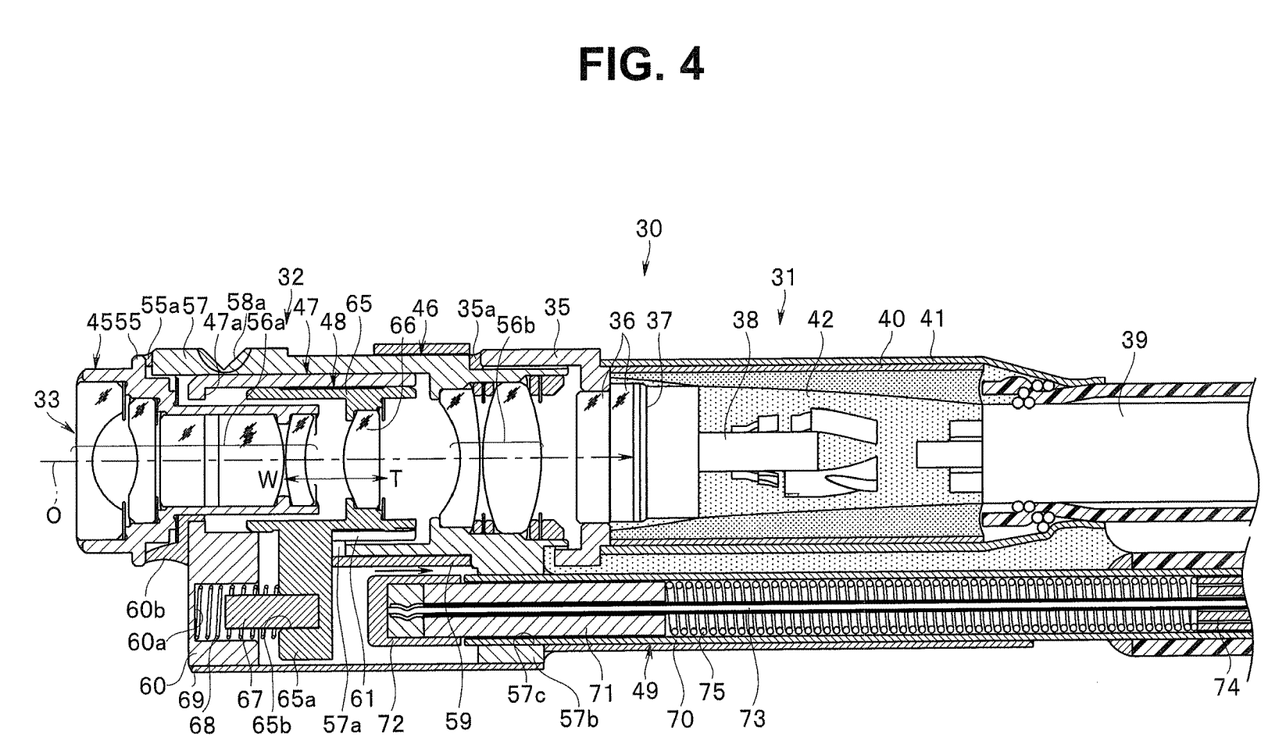
FIG. 4 is a cross-sectional view showing a configuration of the image pickup unit of a state in which the moving lens unit is moved to a back retraction position according to the aspect of the present invention.

As shown in FIGS. 3 and 4, the image pickup unit 30 of the present embodiment includes a solid-state image pickup device unit 31 and an observation optical system unit 32 continuously provided on a distal end side of the solid-state image pickup device unit 31.

The solid-state image pickup device unit 31 includes a solid-state image pickup device holding frame 35, and a front surface side of a solid-state image pickup device chip 37 including a CCD, a CMOS, or the like is held by the solid-state image pickup device holding frame 35 through an optical member 36 such as a cover glass.

A laminated substrate 38 is electrically connected to a back surface side of the solid-state image pickup device chip 37 through an FPC or the like not shown.

A plurality of communication lines branched from a cable 39 are connected to the laminated substrate 38. The cable 39 is inserted and disposed inside of the endoscope 2 and is electrically connected to a video processor through the electrical connector portion 20.

A reinforcing frame 40 is continuously provided on a proximal end outer circumference portion of the solid-state image pickup device holding frame 35, and a heat shrink tube 41 covering up to a distal end part of the cable 39 is provided on an outer circumference of the reinforcing frame 40.

Note that a space formed by the reinforcing frame 40 and the heat shrink tube 41 from a proximal end part of the solid-state image pickup device holding frame 35 is filled with a protective agent 42, such as an adhesive, for holding water tightness of the solid-state image pickup device unit 31 and protecting the solid-state image pickup device unit 31.

The observation optical system unit 32 of the present embodiment includes a bifocal observation optical system 33 configured to move internal lenses back and forth to change an optical characteristic (focal length) to thereby realize the focusing function or the zooming function.

More specifically, the observation optical system unit 32 includes: a front lens group unit 45 positioned on a distal end side; a back lens group unit 46 continuously provided on a proximal end side of the front lens group unit 45; a moving lens position correction frame 47 placed between the front lens group unit 45 and the back lens group unit 46; a moving lens unit 48 that can move back and forth in a photographing optical axis O direction in the moving lens position correction frame 47; and an actuator 49 configured to advance and retract the moving lens unit 48.

Note that the solid-state image pickup device holding frame 35 of the solid-state image pickup device unit 31 is fitted onto the back lens group unit 46 in the observation optical system unit 32, and the back lens group unit 46 and the solid-state image pickup device holding frame 35 are fixed with an adhesive 35a.

The front lens group unit 45 includes: a front lens group frame 55 that is a fixed frame; and a front lens group 56a including a plurality of fixed lenses held by the front lens group frame 55.

The back lens group unit 46 includes: a back lens group frame 57 that is a fixed frame in which a distal end side is fitted onto the front lens group frame 55 and fixed with an adhesive 55a; and a back lens group 56b including a plurality of fixed lenses held on a photographing optical axis O on a proximal end side of the back lens group frame 57.

The solid-state image pickup device holding frame 35 is fitted onto the proximal end side of the back lens group frame 57 and fixed with the adhesive 35a to link the solid-state image pickup device unit 31 and the observation optical system unit 32.

The back lens group frame 57 is provided with a slit 57a penetrating through an inner circumference side and an outer circumference side of the back lens group frame 57. The slit 57a is extended in a same direction as the photographing optical axis O direction, and a distal end side of the slit 57a is opened at a distal end of the back lens group frame 57.

The back lens group frame 57 is provided with a holding rod 57b protruding in an outer diameter direction on a proximal end side of the slit 57a, and the holding rod 57b is provided with an actuator holding hole 57c penetrating in a same axial direction as the photographing optical axis O.

Note that a concave portion 58a that is a screw receiver for receiving the set screw 27 fixed to the distal end rigid member 25 from a lateral direction is formed on an outer circumference portion of the back lens group frame 57.

An adjustment ring 59 for accurately determining a stop position of a proximal end side of the moving lens unit 48 in the photographing optical axis O direction is placed on the back lens group frame 57.

The adjustment ring 59 is configured by a C-shaped ring member in which a width in the photographing optical axis O direction linearly changes in a circumferential direction, and a proximal end is disposed to abut the holding rod 57b here.

The adjustment ring 59 is rotated about the photographing optical axis O along an outer circumference surface of the back lens group frame 57 to change relative positions of a moving lens frame 65 and the holding rod 57b.

As a result, the position of the moving lens frame 65 on the back lens group frame 57 in the photographing optical axis O direction is adjusted.

The moving lens position correction frame 47 is placed between an outer circumference side of the front lens group frame 55 and an inner circumference side of the back lens group frame 57.

Note that an outer diameter of the moving lens position correction frame 47 is greater than an outer diameter of a proximal end part from the middle of the front lens group frame 55 of the front lens group unit 45 introduced and disposed in the back lens group frame 57 of the back lens group unit 46, and the moving lens position correction frame 47 is a substantially cylindrical member that houses the moving lens frame 65 of the moving lens unit 48 to straightly guide the back and forth movement.

A front stopper 60 protruding in the outer diameter direction is provided on a distal end side of the moving lens position correction frame 47.

A spring receiving portion 60a that opens on a back side is provided in a concave shape on the front stopper 60, and a return spring 68 that is a compression spring in which one end is held in the spring receiving portion 60a is wound.

The moving lens position correction frame 47 is provided with a slit 61 penetrating through an inner circumference side and an outer circumference side of the moving lens position correction frame 47. The slit 61 is extended in the same direction as the photographing optical axis O direction to overlap the slit 57a of the back lens group frame 57.

A proximal end side of the slit 61 is opened at a proximal end of the moving lens position correction frame 47. Note that a rib 47a extended in an inner diameter direction is formed on a distal end opening part of the moving lens position correction frame 47.

The moving lens position correction frame 47 is for accurately determining a stop position of a distal end side of the moving lens unit 48 in the photographing optical axis O direction and is fixed to the front lens group frame 55 of the front lens group unit 45 with an adhesive 60b.

The moving lens unit 48 includes: the moving lens frame 65 that is a moving frame; and a moving lens 66 held by the moving lens frame 65.

In the present embodiment, the moving lens frame 65 is arranged in the back lens group frame 57 that is a fixed frame through the moving lens position correction frame 47, and the moving lens frame 65 can move back and forth in the direction along the photographing optical axis O.

The moving lens frame 65 is provided with an operation rod 65a protruding in the outer circumference direction. The operation rod 65a protrudes toward an outer circumference of the back lens group frame 57 through the slit 57a of the back lens group frame 57 and the slit 61 of the moving lens position correction frame 47.

The operation rod 65a is disposed between the front stopper 60 and the holding rod 57b. On the operation rod 65a, a bearing portion 65b facing the spring receiving portion 60a is provided on an opposite surface side of the front stopper 60.

A shaft member 67 protruding in the return spring 68 in the spring receiving portion 60a is held by the bearing portion 65b. The operation rod 65a is biased by biasing force of the return spring 68 toward the holding rod 57b, which is toward the proximal end.

Note that a cover 69 for blocking the slits 57a and 61 in a watertight manner is provided on a tip side of the holding rod 57b, the front stopper 60, and the operation rod 65a.

The actuator 49 includes a guide tube 70 in which a distal end side is held by the actuator holding hole 57c of the holding rod 57b.

The guide tube 70 is provided with a pushrod 71 that can project and recess from a distal end of the guide tube 70, and a head portion 72 as an abutting member that abuts the operation rod 65a in a manner that the head portion 72 can be brought into contact with and separated from the operation rod 65a is fixed to a distal end of the pushrod 71.

A distal end side of a drive wire 73 inserted into the guide tube 70 is linked to the pushrod 71, and a shape memory element 74 made of a shape memory alloy is linked to a proximal end side of the drive wire 73.

In the guide tube 70, a push spring 75 for biasing the pushrod 71 toward the front stopper 60 by biasing force stronger than that of the return spring 68 is further wound around an outer circumference side of the drive wire 73.

The shape memory element 74 is configured to, for example, contract during heating and expand during cooling, and the shape memory element 74 is held in the guide tube 70 such that the shape memory element 74 can be expanded and contracted. A heat source, such as a Peltier element, not shown is provided together with the shape memory element 74, and the heat source can heat or cool the shape memory element 74 according to an operation state of the operation lever 24.

Note that the shape memory element 74 is not limited to the system in which the heat source, such as a Peltier element, is used to heat or cool the shape memory element 74 to expand or contract the shape memory element 74. For example, a system for heating a shape memory alloy by energization to contract the shape memory element 74 can also be adopted.

When the shape memory element 74 is expanded by cooling, the shape memory element 74 causes the drive wire 73 to operate in a direction of release of the biasing force of the push spring 75 (that is, direction of the distal end side along the photographing optical axis O).

As a result, a distal end side of the pushrod 71 is protruded from the guide tube 70 to press the operation rod 65a against the biasing force of the return spring 68 that is a compression spring.

Therefore, the operation rod 65a moves to a position abutting the front stopper 60. Along with the movement of the operation rod 65a, the moving lens frame 65 causes the moving lens 66 to move to an advance position for realizing a preset first focal length (for example, first optical characteristic of wide) (see FIG. 3).

On the other hand, when the shape memory element 74 is contracted by heating, the shape memory element 74 causes the drive wire 73 to operate in a direction against the biasing force of the push spring 75 (that is, direction toward the proximal end along the photographing optical axis O).

As a result, the distal end side of the pushrod 71 is retracted in the guide tube 70. Therefore, the operation rod 65a is biased by the return spring 68 to move to a position abutting the adjustment ring 59.

Along with the movement of the operation rod 65a, the moving lens frame 65 causes the moving lens 66 to move to a retraction position for realizing a preset second focal length (for example, second optical characteristic of tele) (see FIG. 4).

Here, as for the advance position of the moving lens 66 for realizing the first focal length in the image pickup unit 30 configured in this way, relative positions of each fixed frame and the like are adjusted, and the advance position is slightly adjusted by the moving lens position correction frame 47 at the assembly of the solid-state image pickup device unit 31 and the observation optical system unit 32, for example.

More specifically, first, the moving lens position correction frame 47 and the moving lens unit 48 are installed in advance in the back lens group frame 57 of the back lens group unit 46. In a state in which the adjustment ring 59 is fitted into the outer circumference of the back lens group frame 57, optical characteristics based on predetermined design values are checked, and the relative positions of the front lens group unit 45 and the back lens group unit 46 are positioned and fixed by a jig or the like not shown.

Note that the moving lens position correction frame 47 is held at the time by a jig or the like not shown to prevent the moving lens position correction frame 47 from moving from the advance position for realizing the designed and set first focal length (for example, first optical characteristic of wide) that is the stop position of the front side of the moving lens unit 48.

In addition, the front lens group unit 45 and the back lens group unit 46 are held by a jig not shown in a state in which axis alignment is performed such that optical central axes in the photographing optical axis O coincide, because the lens power of the lens groups 56a and 56b of the front lens group unit 45 and the back lens group unit 46 is large.

From this state, the front lens group frame 55 of the front lens group unit 45 and the back lens group frame 57 of the back lens group unit 46 are fixed to each other with the adhesive 55a.

Note that the front lens group unit 45 has an outer diameter that provides a clearance in the back lens group unit 46 when the front lens group unit 45 is fitted to the back lens group unit 46, and the moving lens unit 48 and the moving lens position correction frame 47 are disposed in the clearance formed between the back lens group unit 46 and the front lens group unit 45.

That is, the front lens group frame 55 of the front lens group unit 45 has an outer diameter smaller than inner diameters of the back lens group frame 57 of the back lens group unit 46, the moving lens frame 65 of the moving lens unit 48, and the moving lens position correction frame 47.

Next, relative positions of the back lens group frame 57 of the back lens group unit 46 and the solid-state image pickup device holding frame 35 of the solid-state image pickup device unit 31 are positioned and fitted by a jig or the like not shown, while the optical characteristics based on predetermined design values are checked.

From this state, the back lens group frame 57 of the back lens group unit 46 and the solid-state image pickup device holding frame 35 are fixed to each other by the adhesive 35a.

Next, when the moving lens position correction frame 47 held by the jig or the like not shown coincides with the advance position for realizing the first focal length (for example, first optical characteristic of wide) set while checking the optical characteristics, the adhesive 60b is used to fix the moving lens position correction frame 47 to the front lens group frame 55 of the front lens group unit 45 at the position.

Note that when the moving lens position correction frame 47 is displaced from the advance position for realizing the set first focal length (for example, first optical characteristic of wide) as a result of checking the optical characteristics, the moving lens position correction frame 47 is slightly adjusted forward and backward along the photographing optical axis O and fixed to the front lens group frame 55 of the front lens group unit 45 with the adhesive 60*b*.

That is, in the state in which the operation rod 65*a* of the moving lens unit 48 is in contact with the front stopper 60 of the moving lens position correction frame 47, the front lens group frame 55 and the moving lens position correction frame 47 are fixed through the adhesive 60*b* while the optical characteristics are checked.

By the way, the moving lens position correction frame 47 is also fixed to the back lens group frame 57 through the adhesive, in addition to the front lens group frame 55.

As shown in FIGS. 5 and 6, the moving lens position correction frame 47 includes plate-shaped guide portions 60*c* on both side parts, the guide portions 60*c* extended along the slit 61 in the proximal end direction from the front stopper 60 and straightly guiding the moving lens frame 65 of the moving lens unit 48. Concave portions 47*b* for potting a resin (adhesive) are formed on outer surfaces of the guide portions 60*c*.

As shown in FIGS. 7 and 8, the concave portions 47*b* formed on the guide portions 60*c* of the moving lens position correction frame 47 are in an exposed state without being hidden by the back lens group frame 57 in the state in which the front lens group frame 55 of the front lens group unit 45 and the back lens group frame 57 of the back lens group unit 46 are fixed to each other with the adhesive 55*a*. Note that FIGS. 7 and 8 depict a state in which the solid-state image pickup device holding frame 35 of the solid-state image pickup device unit 31 is not illustrated.

The concave portions 47*b* formed on the guide portions 60*c* of the moving lens position correction frame 47 are then potted with the adhesive 57*b* (see FIG. 9). The adhesive 57*b* potted in the concave portions 47*b* enters a minute gap formed between an outer circumference surface of the moving lens position correction frame 47 and an inner circumference surface of the back lens group frame 57 as shown in FIG. 9 and flows as indicated by arrows in FIG. 9 due to a capillary phenomenon. The adhesive 57*b* is supplied between the moving lens position correction frame 47 and the back lens group frame 57 in the circumferential direction of the cylindrical portion.

As a result, compared to a typical structure of bonding and fixing only parts that can be viewed from the outside, that is, a structure of bonding and fixing only the parts that can be viewed from the outside between the moving lens position correction frame 47 and the front lens group frame 55 here, the adhesive 57*b* is also supplied to parts that cannot be viewed from the outside of the moving lens position correction frame 47 and the back lens group frame 57, and the parts can be bonded and fixed.

Therefore, the moving lens position correction frame 47 can be firmly bonded to the front lens group frame 55 and the back lens group frame 57 in the image pickup unit 30 of the present embodiment. As a result, the image pickup unit 30 can prevent a position displacement of the moving lens position correction frame 47 generated by a load during the assembly and a position displacement of the moving lens position correction frame 47 caused by a load during the use by a user and can prevent a displacement of the optical characteristics set during the assembly and the use.

Next, the moving lens unit 48 is slightly adjusted to the retraction position for realizing the second focal length (for example, second optical characteristic of tele) set in advance that is the stop position of the back side of the moving lens unit 48, and the moving lens unit 48 is positioned by rotating and operating the adjustment ring 59 while the optical characteristics are checked. The moving lens unit 48 is fixed through an adhesive or the like.

That is, in the state in which the operation rod 65*a* of the moving lens unit 48 abuts the adjustment ring 59, the adjustment ring 59 is rotated and operated relative to the back lens group frame 57, and the retraction position of the moving lens unit 48 is determined while the optical characteristics are checked. The adjustment ring 59 is fixed to the back lens group frame 57 through an adhesive or the like.

According to the embodiment, on the front and the back, the abutment of the front stopper 60 and the adjustment ring 59 of the moving lens position correction frame 47 and the operation rod 65*a* restricts the movement of the moving lens frame 65 toward the advance side and the retraction side along the photographing optical axis O, and the movement of the moving lens unit 48 is stopped at the position for realizing the first focal length and the second focal length. This can obtain a high-quality picked-up image by preventing a displacement of the set optical movement position and axis of the moving lens 66 held by the moving lens frame 65.

That is, in the image pickup unit 30 of the present embodiment, the moving lens unit 48 moves back and forth in the moving lens position correction frame 47 provided in the back lens group unit 46, and the operation rod 65*a* of the moving lens unit 48 comes in surface contact and abuts the front stopper 60 of the moving lens position correction frame 47.

Therefore, the image pickup unit 30 can prevent degradation of an image because, for example, an axis displacement of the moving lens 66 due to a tilt of the moving lens frame 65 of the moving lens unit 48 is prevented, particularly at the advance position for realizing the first optical characteristic of wide.

Furthermore, in the image pickup unit 30, the position for restricting the movement of the moving lens frame 65 toward the advance side and the retraction side along the photographing optical axis O can be slightly adjusted and corrected by the front stopper 60 and the adjustment ring 59 of the moving lens position correction frame 47, after the front lens group frame 55 of the front lens group unit 45 and the back lens group frame 57 of the back lens group unit 46 are fixed with the adhesive 55*a*.

As a result, in the image pickup unit 30, the advance position and the retraction position for stopping the moving lens unit 48 can be easily set by slightly adjusting the moving lens position correction frame 47 and the adjustment ring 59 to satisfy the predetermined optical characteristics, even if there are a focus displacement during curing of the adhesive 55*a* for fixing the front lens group frame 55 of the front lens group unit 45 and the back lens group frame 57 of the back lens group unit 46 and a focus displacement during curing of the adhesive for fixing the back lens group frame 57 and the solid-state image pickup device frame 35.

Furthermore, in the image pickup unit 30, the advance position and the retraction position for stopping the moving lens unit 48 can be easily set by slightly adjusting the moving lens position correction frame 47 and the adjustment ring 59 to satisfy predetermined optical characteristics, even if assembly accuracy of the front lens group unit 45, the back lens group unit 46, and the solid-state image pickup device unit 31 is required along with miniaturization (shrinking) of an image pitch of the solid-state image pickup device chip 37. As a result, a yield rate of the image pickup unit 30 is also improved.

According to the description, the image pickup unit 30 and the endoscope 2 of the present embodiment can obtain a high-quality picked-up image by preventing an axis displacement of the moving lens frame 65 (moving lens 66) of the moving lens unit 48.

The image pickup unit 30 uses the abutment position of the moving frame using the correction frame only for the slight correction when there is a displacement. Therefore, the power balance of the optical system is not lost compared to when the moving frame is used to adjust the image quality, and thus, the image pickup unit 30 can also prevent affecting the image quality, such as angle of view and aberration.

Furthermore, the strength of the moving lens position correction frame 47 is increased by forming the rib 47a extended in the inner diameter direction on the distal end opening part. This can prevent deformation from the lateral side during the fixation of the back lens group unit 46 with the jig and during the fixation to the distal end rigid member 25 through the set screw 27.

In addition, the formation of the rib 47a can prevent the adhesive 55a after the completion of the image pickup unit 30 from flowing out toward the moving lens frame 65 under a high temperature environment in post-process and can prevent poor abutment, poor sliding, and the like on the front side of the moving lens 66.

As a result, the moving lens unit 48 sliding in the moving lens position correction frame 47 can be smoothly advanced and retracted.

Furthermore, the rib 47a of the moving lens position correction frame 47 may be formed to abut the distal end of the moving lens unit 48 according to the position where the operation rod 65a of the moving lens unit 48 comes into surface contact and abuts the front stopper 60.

This can more surely stop the moving lens unit 48 at the advance position of the first focal length without an axis displacement.

Modification

By the way, the concave portion 58a that is a screw receiver for receiving the set screw 27 fixed to the distal end rigid member 25 from the lateral direction is formed on the outer circumference portion of the back lens group frame 57 as shown in FIG. 10.

In addition, the back lens group frame 57 may be provided with a concave portion 58b that is a jig receiver for fixing the jig and notches 58c, such as marking-off, on the outer circumference portion. Note that the concave portion 58 that is a screw receiver may also be used as a jig receiver.

In this way, when the concave portions 58a and 58b, the notches 58c, and the like are provided on the back lens group frame 57, the fixation of the back lens group frame 57 with the jig becomes simple, and assembly and positioning on the front lens group frame 55, the solid-state image pickup device holding frame 35, and the like can be more accurately performed.

Note that the jig receiver is not limited to the concave shape, and the jig receiver can have a shape, such as a planar shape, that allows simple fixation by the jig.

Furthermore, the notches 58c may be indicator portions for distinguishing various products of the image pickup unit 30 with different angles of view. This allows an operator to easily figure out the type of the observation optical system unit 32 flowing through a manufacturing line during the assembly of the image pickup unit 30.

Note that the present invention is not limited to each embodiment and each modification described above, and various modifications and changes can be made. The modifications and the changes are also within the technical scope of the present invention. For example, it is obvious that the configurations of each embodiment and each modification described above may be appropriately combined.

Although an example of applying the image pickup unit to the endoscope is described in each embodiment and the like described above, the present invention is not limited to this, and it is obvious that the image pickup unit can also be applied to other electronic devices and the like.

According to the image pickup unit and the endoscope of the present invention, an axis displacement of the moving lens frame can be prevented, and a high-quality picked-up image can be obtained in the focus switching type observation optical system.

What is claimed is:

1. An image pickup unit comprising:
   an observation optical system comprising a fixed lens and a moving lens, the fixed lens comprising a front lens group and a back lens group, the observation optical system being capable of setting two focal lengths;
   a front lens group frame that holds the front lens group;
   a back lens group frame that holds the back lens group, the back lens group frame holding the front lens group frame at a distal end of the back lens group frame;
   a correction frame disposed on an inner circumference surface of the back lens group frame;
   a moving frame that is disposed to be movable on an inner circumference surface of the correction frame along an optical axis of the observation optical system, the moving frame holding the moving lens;
   a holding rod provided to the back lens group frame, the holding rod protruding in an outer diameter direction; and
   an operation rod provided to the moving frame, the operation rod protruding in the outer diameter direction, the operation rod being applied with a driving force of the moving frame from an actuator, wherein
   the front lens group frame and/or the back lens group frame and the correction frame are fixed to each other with an adhesive, and
   the operation rod contacts the holding rod to restrict the moving frame from moving toward a distal end side and defines one of the two focal lengths of the observation optical system.

2. The image pickup unit according to claim 1, wherein the front lens group frame having an outer diameter smaller than inner diameters of the back lens group frame, the moving frame, and the correction frame is introduced and fixed in the back lens group frame.

3. The image pickup unit according to claim 1, wherein a jig receiver for fixation during assembly is formed on an outer circumference of the fixed frame.

4. The image pickup unit according to claim 1, wherein the correction frame comprises a rib abutting the moving frame and extended in an inner diameter direction according to a position where the stopper restricts movement of the moving frame.

5. The image pickup unit according to claim 1, wherein the correction frame comprises a guide portion configured to straightly guide the moving frame, and
   a concave portion for potting a resin for bonding the correction frame and the fixed frame is formed on the guide portion.

6. An endoscope comprising the image pickup unit according to claim 1 on a distal end portion of an insertion portion inserted into a subject.

7. The image pickup unit according to claim 1, wherein the back lens group frame is provided with an adjustment ring, and the operation rod contacts the adjustment ring to restrict the moving frame from moving toward a proximal end side and defines an other of the two focal lengths of the observation optical system.

\* \* \* \* \*